(12) United States Patent
Chambers

(10) Patent No.: US 11,235,117 B2
(45) Date of Patent: Feb. 1, 2022

(54) TRACHEAL TUBES

(71) Applicant: SMITHS MEDICAL INTERNATIONAL LIMITED, Ashford (GB)

(72) Inventor: Steve Chambers, Hythe (GB)

(73) Assignee: SMITHS MEDICAL INTERNATIONAL LIMITED, Ashford (GB)

(*) Notice: Subject to any disclaimer, the term of this patent is extended or adjusted under 35 U.S.C. 154(b) by 860 days.

(21) Appl. No.: 15/112,785

(22) PCT Filed: Dec. 24, 2014

(86) PCT No.: PCT/GB2014/000529
§ 371 (c)(1),
(2) Date: Jul. 20, 2016

(87) PCT Pub. No.: WO2015/110775
PCT Pub. Date: Jul. 30, 2015

(65) Prior Publication Data
US 2016/0331919 A1 Nov. 17, 2016

(30) Foreign Application Priority Data
Jan. 24, 2014 (GB) .................... 1401231

(51) Int. Cl.
A61M 16/04 (2006.01)

(52) U.S. Cl.
CPC .... A61M 16/0445 (2014.02); A61M 16/0463 (2013.01); A61M 16/0465 (2013.01); *A61M 2207/00* (2013.01); *A61M 2250/00* (2013.01)

(58) Field of Classification Search
CPC .......... A61M 16/0445; A61M 16/0463; A61M 16/0465; A61M 2207/00
See application file for complete search history.

(56) References Cited

U.S. PATENT DOCUMENTS

| 4,596,248 A * | 6/1986 | Lieberman ........ A61M 16/0475 128/207.16 |
| 8,225,795 B2 | 7/2012 | Pell |
| 8,499,763 B2 * | 8/2013 | Ledwith ............ A61M 16/0463 128/200.24 |

(Continued)

FOREIGN PATENT DOCUMENTS

| GB | 2 324 248 | 10/1998 |
| GB | 2324248 A * | 10/1998 ............ A61M 25/10 |

(Continued)

OTHER PUBLICATIONS

PCT International Search Report (PCT/ISA/210) and Written Opinion (PCT/ISA/237) ISA/EP, PCT/GB2014/000529, dated Mar. 3, 2015.

*Primary Examiner* — Samchuan C Yao
*Assistant Examiner* — Cana A Gallegos
(74) *Attorney, Agent, or Firm* — Louis Woo

(57) ABSTRACT

The sealing cuff (10) on a tracheal tube has a collar (31) at its patient end inverted within the inflatable part (32) of the cuff and attached with the shaft 1 immediately adjacent its patient end (6). The cuff (10) has a patient end region (33) of frusto-conical shape inclined to the axis of the shaft at about 30° and extending by about half the length of the inflatable portion.

9 Claims, 2 Drawing Sheets

(56) References Cited

U.S. PATENT DOCUMENTS

| | | | | |
|---|---|---|---|---|
| 2007/0295337 A1* | 12/2007 | Nelson | ............. | A61M 16/04 |
| | | | | 128/207.15 |
| 2009/0241964 A1* | 10/2009 | Aljuri | ............. | A61B 17/12104 |
| | | | | 128/207.15 |
| 2011/0083672 A1 | 4/2011 | Webster et al. | | |
| 2012/0103341 A1* | 5/2012 | Behlmaier | ........ | A61M 16/0465 |
| | | | | 128/207.14 |
| 2012/0220845 A1* | 8/2012 | Campbell | ............. | A61B 5/0836 |
| | | | | 600/364 |
| 2013/0133644 A1* | 5/2013 | Rosekrans | ........ | A61M 16/0465 |
| | | | | 128/200.26 |

FOREIGN PATENT DOCUMENTS

| | | | | | |
|---|---|---|---|---|---|
| GB | 2344528 A | * | 6/2000 | ............ | A61M 16/04 |
| WO | WO 2007/149202 | | 12/2007 | | |

\* cited by examiner

TRACHEAL TUBES

This invention relates to tracheal tubes of the kind having a shaft and an inflatable sealing cuff on its outside towards its patient end that is adapted, during use, to provide a seal with the tracheal wall, the cuff being attached with the shaft by means of collars at opposite ends.

Tracheal tubes are used to supply ventilation and anaesthetic gases to a patient, such as during surgery. The tracheal tube may be inserted via the mouth or nose, in the case of an endotracheal tube, or may be inserted via a surgically-made tracheostomy opening in the neck, in the case of a tracheostomy tube. Most, but not all, tracheal tubes have some form of a seal on their outside which forms a seal between the outside of the tube and the inside of the trachea so that gas flow is confined to the bore of the tube and cannot flow around the outside of the tube, between the tube and the trachea. The most common form of seal is provided by an inflatable cuff that is inflated and deflated via a small bore lumen extending rearwardly along the tube and connected towards its rear end to an inflation line terminated by an inflation indicator, valve and connector. These inflatable cuffs may be of the high-volume/low-pressure kind where the cuff is formed of a flexible material moulded with a natural annular or doughnut shape that is inflated without stretching by relatively low-pressure gas supplied via the inflation line. Alternatively, the cuff may be of the low-volume/high-pressure kind where the cuff is of an elastic material that lies close to the tube shaft when uninflated but is inflated and stretched to a larger diameter by relatively high pressure gas supplied via the inflation line. Cuffs of differing shapes and configurations are described, for example, in U.S. Pat. No. 7,987,851, GB2356571, U.S. Pat. Nos. 8,307,830 and 8,434,488.

One problem with tracheal tubes, especially tracheostomy tubes, is that the tip of the tube may contact the tracheal wall during use and cause damage to the tracheal tissue.

It is an object of the present invention to provide an alternative tracheal tube.

According to the present invention there is provided a tracheal tube of the above-specified kind, characterised in that at least the collar at the patient end is inverted within the inflatable portion of the cuff so that it does not extend beyond the inflatable portion of the cuff, that the patient end collar is attached with the shaft immediately adjacent the patient end of the shaft so that substantially no part of the shaft protrudes from the inflatable portion of the cuff, and that the cuff has an inflated shape with a tapering substantially frusto-conical profile at a patient end region.

The sealing cuff preferably has a tapering region at its machine end and a substantially cylindrical region intermediate the patient and machine end tapering regions. The tapering region at the machine end of the cuff preferably inclines at a steeper angle than the patient end tapering region. The tapering region at the machine end of the cuff preferably inclines at an angle to the shaft of about twice the angle of the patient end region. The tapering patient end region of the cuff preferably extends at an angle of about 30° to the axis of the shaft. The sealing cuff may be of the high-volume/low-pressure kind. The collar at the machine end of the cuff may be attached with the shaft outside the inflatable portion of the cuff. The tapering patient end region of the cuff preferably occupies about half the length of the inflatable portion of the cuff.

A tracheostomy tube according to the present invention will now be described, by way of example, with reference to the accompanying drawings, in which.

Figure 1:
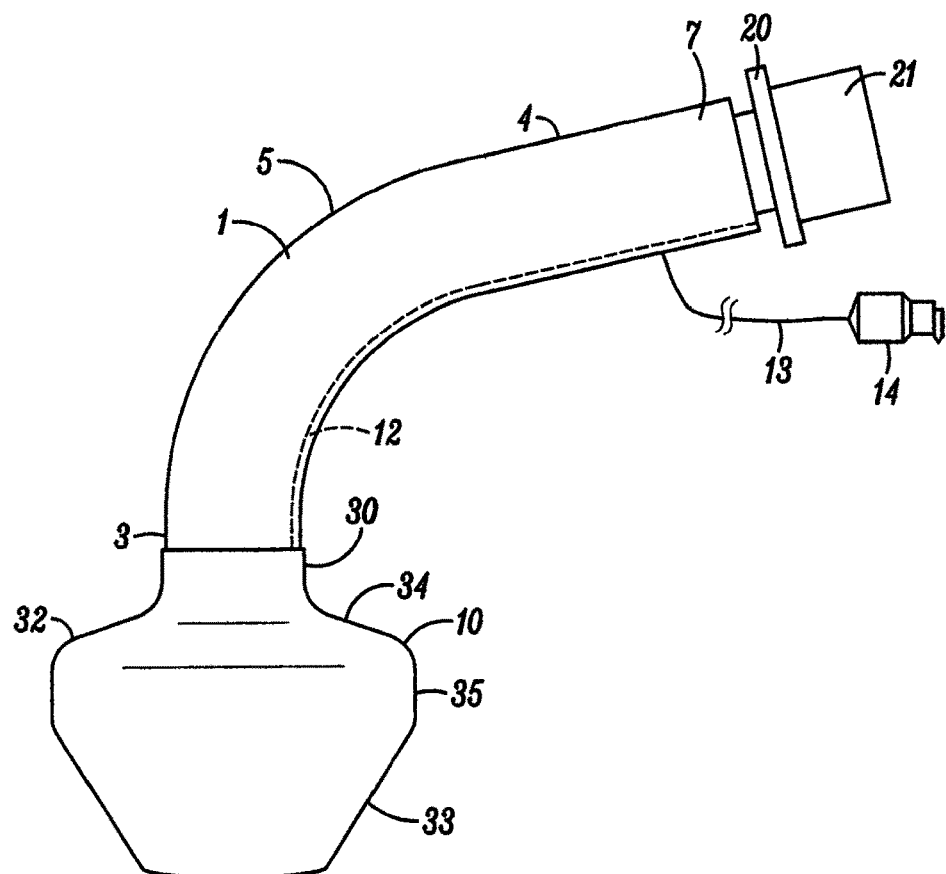
FIG. 1 is a side elevation view of the tube.
Figure 2:
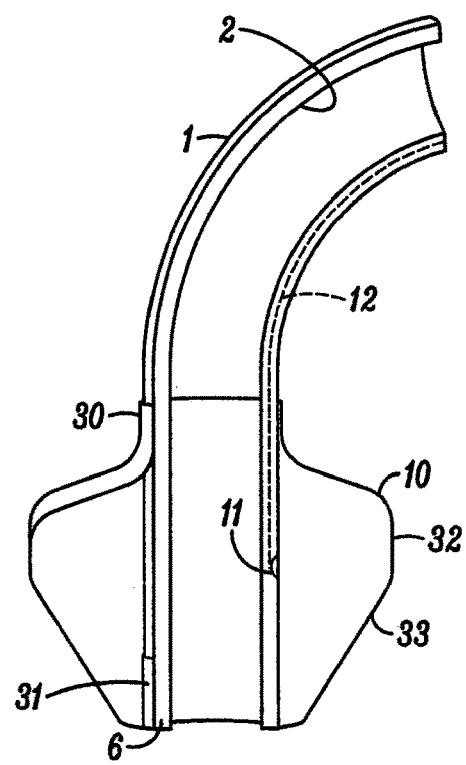
FIG. 2 is an enlarged perspective cross-sectional view through the patient end of the tube shown in FIG. 1.

With reference to FIGS. 1 and 2, the tracheostomy tube includes a tubular shaft 1 having a bore 2 extending along its length. The tube is formed with a relatively straight patient end portion 3 and a relatively straight machine end portion 4 linked by a curved intermediate portion 5 so that the patient and machine ends 6 and 7 are angled at about 100° to one another. The shaft 1 is extruded or moulded from a plastics material such as PVC or silicone. Towards its patient end 6 the tube has sealing means provided by an inflatable cuff 10 embracing the shaft 1. The cuff 10 is of the high-volume/low-pressure kind so that it has a relatively floppy shape when deflated but, when inflated, it fills out at low pressure to a diameter just larger than the internal diameter of the trachea, so that it contacts the inside of the trachea with low pressure. The cuff 10 is moulded to the desired inflated shape from a plastics material such as PVC or polyurethane. The cuff 10 is attached to the shaft 1 at opposite ends over an opening 11 on the outer surface of the shaft into an inflation lumen 12 extending along the shaft within its wall thickness. The inflation lumen 12 is connected towards the rear end 7 of the tube with a small-bore inflation line 13 that is terminated by a combined inflation indicator, valve and connector 14.

At its rear, machine end 7 the tube has a flange 20, to which a neck strap (not shown) is attached, and a standard 15 mm female coupling 21.

The tube may have a conventional, removable inner cannula (not shown).

The cuff 10 is attached to the outside of the shaft 1 by a machine end collar 30 and a patient end collar 31. The machine end collar 30 is attached to the shaft 1 in the usual way, by extending the collar externally beyond the inflatable portion 32 of the cuff 10 and bonding its inner surface to the outside of the shaft, such as with an adhesive or solvent or by a heat bonding method.

The patient end collar 31, however, is attached in a different manner in that it is inverted within the inflatable portion 32 and the original outer surface of the collar is bonded to the outside of the shaft 1. In this way, patient end collar 31 does not extend beyond the inflated portion 32 of the cuff 10.

It would be possible for the machine end collar of the cuff also to be inverted inside the inflated portion, in the manner described in U.S. Pat. No. 5,201,310, especially if the tube had a suction line for aspirating secretions that collect above the cuff.

The inflated portion 32 of the cuff 10 has three regions, namely a patient end region 33, a machine end region 34 and an intermediate region 35. The patient end region 33 occupies about half the length of the inflated portion 32 and has a tapering conical or frusto-conical shape with a diameter increasing away from the patient end 6 of the shaft 1, extending at an angle of about 30° to the axis of the shaft. The patient end region 33 need not be an exact frusto-conical shape but could be curved slightly outwardly to give it a bullet shape, or slightly inwardly to give it a slightly flared shape. The intermediate region 35 adjoins the rear of the patient region 33 and occupies about a quarter of the length of the inflated portion 32. The intermediate region 35 has a substantially constant diameter along its length and a cylindrical shape. The machine end region 34 occupies about one quarter of the length of the inflated portion 32 and extends between the rear end of the intermediate region 35 and the forward end of the machine end collar 30. The machine end region 34 has a conical or frusto-conical shape and is angled more steeply to the shaft 1 than the patient end region 33, at an angle of about twice that of the patient end region at about 60° to the shaft 1. The cuff 10, therefore, has an asymmetric shape along its length. The shape of the cuff 10 described above is the shape when inflated outside the trachea, that is, without constraint. It will be appreciated that, when the cuff 10 is inflated inside the trachea its shape will differ slightly from that described and illustrated.

Figure 3:
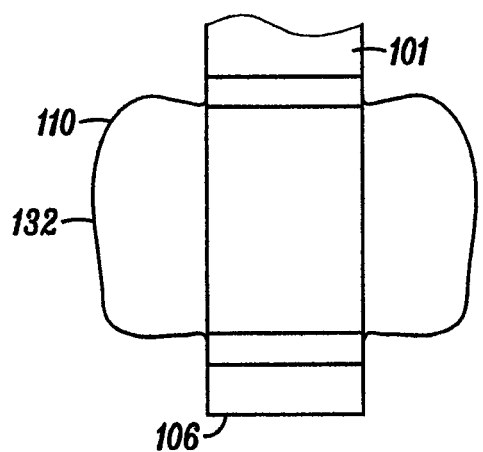
FIG. 3 is a side elevation view of the patient end of a prior art tube.

The patient end collar 31 is attached with the outside of the shaft 1 closely adjacent its patient end 6, that is, within about 1 mm of its patient end so that the inflated portion 32 of the cuff extends right to the patient end of the shaft or to within about 1 mm of this. This arrangement ensures that the patient end 6 of the shaft 1 is protected from contact with the tracheal wall during use by the patient end of the inflated cuff 10, which acts as a bumper around the end of the shaft. If a conventional cuff 110 of the symmetrical, doughnut shape shown in FIG. 3 were located right at the patient end 106 of the shaft 101 there would be a possible risk that the inflated part 132 of the cuff could extend beyond the end of the shaft and occlude the passage to the shaft. This risk would be increased where the cuff 110 was inflated at low pressure and force was applied to pull the shaft 101 outwardly of the patient since it would tend to roll the patient end of the cuff forwardly relative to the patient end 106 of the shaft. For this reason the inflatable portion 132 of these conventional shape cuffs 110 are always spaced from the patient end 106 of the shaft 101 by at least about 5 mm, as illustrated in FIG. 3. By contrast, the tapered shape of the patient region 33 of the cuff 10 of the present invention cannot be displaced forwardly relative to the shaft 1 to the same extent and thereby enables the patient end 6 of the shaft to be protected by the cuff without risk of occlusion.

The invention could be used in any tracheal tube, not just tracheostomy tubes, and is not limited to tubes for human use but could be used on veterinary tracheal tubes.

The invention claimed is:

1. A tracheostomy tube comprising:
a shaft including a patient end and a cuff having an inflatable portion on an outside surface of the shaft towards the patient end that is adapted, during use, to provide a seal with the tracheal wall, the cuff being attached to the shaft by means of a patient end collar and a machine end collar, the shaft being a tubular shaft having a bore extending along its length, the bore adapted to receive a removable inner cannula, wherein at least the patient end collar is inverted within the inflatable portion of the cuff so that it does not extend beyond the inflatable portion of the cuff, and wherein the patient end collar is attached to the outside surface of the shaft immediately adjacent the patient end of the shaft so that substantially no part of the shaft protrudes from the inflatable portion of the cuff and that the cuff has an inflated shape with a tapering substantially frusto-conical profile at a patient end region such that the inflated portion of the cuff only extends substantially right to the patient end of the shaft so as not to extend beyond the patient end of the shaft.

2. A tracheotomy tube according to claim 1, characterized in that the cuff has a tapering region at its machine end and a substantially cylindrical region intermediate the patient end region and the tapering region.

3. A tracheotomy tube according to claim 2, characterized in that the tapering region at the machine end of the cuff inclines at a steeper angle than the tapering at the patient end region.

4. A tracheotomy tube according to claim 3, characterized in that the tapering region at the machine end of the cuff inclines at angle to the shaft of about twice the angle of the patient end region.

5. A tracheotomy tube according to claim 1, characterized in that the tapering at the patient end region of the cuff extends at an angle to the axis of the shaft.

6. A tracheotomy tube according to claim 1, characterized in that the cuff is of the high-volume/low-pressure kind.

7. A tracheotomy tube according to claim 1, characterized in that the machine end collar of the cuff is attached to the shaft outside the inflatable portion of the cuff.

8. A tracheotomy tube according to claim 1, characterized in that the tapering at the patient end region of the cuff is along a portion of the length of the inflatable portion of the cuff.

9. A tracheostomy tube comprising:
a tubular shaft having a through bore extending between a patient end and a machine end having a flange adapted to have a neck strap attached thereto, the bore adapted to receive a removable inner cannula;
a cuff having an inflatable portion on an outside surface of the shaft towards the patient end that is adapted, during use, to provide a seal with the tracheal wall, the cuff being attached to the shaft by means of a patient end collar and a machine end collar,
wherein at least the patient end collar is inverted within the inflatable portion of the cuff so that it does not extend beyond the inflatable portion of the cuff, the patient end collar attached to the outside surface of the shaft immediately adjacent the patient end of the shaft so that substantially no part of the shaft protrudes from the inflatable portion of the cuff, and
wherein when the cuff is inflated, the cuff has an inflated shape with a tapering substantially frusto-conical profile at a patient end region such that the inflated portion of the cuff only extends substantially right to the patient end of the shaft so as not to extend beyond the patient end of the shaft.

\* \* \* \* \*